United States Patent [19]

Ron et al.

[11] Patent Number: 5,010,167

[45] Date of Patent: Apr. 23, 1991

[54] POLY(AMIDE-AND IMIDE-CO-ANHYDRIDE) FOR BIOLOGICAL APPLICATION

[75] Inventors: Eyal Ron, Lexington; Andrea Staubli, Belmont; Robert S. Langer, Newton, all of Mass.

[73] Assignee: Massachusetts Institute of Technology, Cambridge, Mass.

[21] Appl. No.: 331,432

[22] Filed: Mar. 31, 1989

[51] Int. Cl.$^5$ .............................................. C08G 69/10
[52] U.S. Cl. .................................. 528/328; 525/54.1; 528/310; 606/230; 606/231
[58] Field of Search ................................ 528/328, 310

[56] References Cited

PUBLICATIONS

Rosen, et al., *Biomaterials* 4, 131-133 (1983).
Leong, et al., *J. Biomedical Res.* 19, 941-955 (1985) and 20, 51-64 (1986).
Kohm, et al., *J. Immunological Methods* 95, 31-38 (1986).
Domb, et al., *Macromolecules* 21, 1925-1929 (1988).
Pierschbacher, et al., *Proc. Natl. Acad. Sci. USA* 80, 1224-1227 (1983).
Pierschbacher, et al., *Proc. Natl. Acad. Sci. USA* 81, 5985-5988 (1984).
Pierschbacher, et al., "Cell Attachement Activity of Fibronectin can be Duplicated by Small Synthetic Fragments of the Molecule", (No Cite But Accepted for Publication in 1984).
Vacanti, e tal., *J. Pediatric Surgery* 23 (1), 3-9 (1988).
Sidman, et al., *J. Membrane Sci.* 7, 277-291 (1980).
Kohn and Langer, *J. Am. Chem. Soc.* 109, 817-820 (1987).
Gonzales, et al., *Die Angewandte Makromolekulare Chemie* 55, 85-96 (1976).
Jpn. Kokai Tokkyo Koho 81 12,351 Published 1981 *Chem. Abstracts* 95: 62702a (1981).
Abajo, et al., *Die Angewandte Makromolekulare Chemie* 19, 121-134 (1971).
Nefkens, et al., *Recueil* 79, 689-699 (1960).
Hoogwater, et al., *Recueil* 92, 819-825 (1973).

*Primary Examiner*—Harold D. Anderson
*Attorney, Agent, or Firm*—Kilpatrick & Cody

[57] ABSTRACT

Biocompatible, biodegradable poly(amide- and imide-co-anhydride)s are described which are useful for biological applications such as biodegradable controlled release devices for drug delivery, site-specific drug carriers, matrices for cell attachment, and for bioabsorbable sutures.

4 Claims, No Drawings

POLY(AMIDE-AND IMIDE-CO-ANHYDRIDE) FOR BIOLOGICAL APPLICATION

BACKGROUND OF THE INVENTION

This invention relates to the preparation and use of poly(amide-co-anhydrides) and poly(imide-co-anhydrides).

Various types of polymers have been tested for use in forming a biodegradable, biocompatible drug delivery device, including poly(esters), poly(amides), poly(urethanes), poly(orthoesters), poly(acrylonitriles), poly(phosphazenes) and poly(anhydrides). Biodegradable controlled release systems for drugs or other biologically active compounds have an advantage over other controlled release systems in obviating the need to surgically remove the non-biodegradable drug depleted device since the biodegradable device degrades as the biologically active compound is released.

The polymer's erosion characteristics in an aqueous media is of particular importance in choosing a polymer for controlled delivery. When water penetrates a device made of a polymer having water labile bonds, hydrolytic degradation occurs internally, forming channels in the device. Thus, in addition to release of incorporated drug from the exterior of the device through surface erosion, there is also internal erosion and uncontrolled bulk release of the drug through channels formed in the device. Release of drug is more controlled, however, when the rate of hydrolytic degradation on the surface of the polymeric device is much faster than the rate of water penetration into the bulk of the matrix. Accordingly, surface eroding polymers are preferred for applications where continuous release over a controlled period of time is required.

Poly(anhydrides) surface erode in vivo due to hydrolysis, rather than by enzymatic degradation. As a result there are fewer variations in the rate of drug release from individual to individual using a poly(anhydride) controlled delivery device than one which degrades enzymatically. Furthermore, poly(anhydride) degradation products are nonmutagenic, noncytotoxic, and have a low teratogenic potential, as discussed by Leong, K. W., D'Amore, P. D., Marletta, M. and Langer, R., *J. Biomed. Mater. Res.* 20, 51 (1986). These polymers are soluble in common organic solvents (40% w/v) and have low melting points, generally in the range of 40°-100° C., which facilitates fabrication into controlled delivery devices.

The hydrolytic degradation rates of poly(anhydrides) can be altered several thousandfold by simple changes in the polymer backbone, for example, by choosing the appropriate monomers, as shown by Domb and Langer, *J. Poly. Sci.*, 27, 1 (1987). As described in copending application Ser. No. 080,631 entitled "Polyanhydrides with Improved Hydrolytic Degradation Properties" filed July 31, 1987 by Domb and Langer, poly(anhydrides) with a uniform distribution of alkyl and aromatic residues display zero-order kinetic profiles over various periods of time (days to months), indicating that surface erosion rather than bulk erosion is occurring.

In order to provide even greater control over the rate of release of compound from the device, it would be advantageous if a controlled delivery device could be fabricated from polymers containing the material to be delivered as an integral part of the polymeric matrix, as compared to being encapsulated within the matrix. It would be particularly useful if polymers could be formed from peptides or peptide derivatives, many of which have important biological activity, such as hormones.

Previous attempts to make biodegradable drug delivery devices from synthetic poly(amino acids) have suffered from several problems. One major problem is the antigenicity of polymers containing more than three amino acids, provoking an inflammatory response. Another problem is in device fabrication since poly(amino acids) are insoluble in common organic solvents and have high melting points due to the peptide backbone. Further, these polymers generally absorb significant amounts of water which can be deleterious to incorporated substances within the polymer, and alter degradation and release characteristics. Still another problem is the cost of synthesis of the poly(amino acids). For example, high molecular weight poly(amino acids) are often prepared from N-carboxy-anhydrides which are expensive to synthesize even if they are derived from inexpensive amino acids. Finally, poly(amino acids) are enzymatically, not hydrolytically, degraded in vivo, which can result in variations in the rate of degradation and release from individual to individual, as well as in the same person over time due to the changing nature of the cellular response to these materials.

Several efforts have been made to modify poly(amino acids) to overcome these limitations. Sidman, et al., reported in *J. Memb. Sci.* 7, 277 (1980), that rods formed from copolymers of L-glutamic acid and gamma-ethyl-L-glutamate degraded slowly in vivo, typically over a period of six months. As reported in *J. Am. Chem. Soc.* 109, 817 (1987), Kohn and Langer synthesized pseudo poly(amino acids) by polymerizing α-L-amino acids or dipeptides through non-amide bonds, such as ester and iminocarbonate located on the amino acid side chains, rather than at the amino acid termini. These polymers also degrade slowly.

It is therefore an object of the present invention to prepare biodegradable polymers which are made of biologically active compounds, especially peptides and peptide derivatives, which can be released in vivo with activity, without provoking an inflammatory response.

It is a further object of the present invention to prepare biodegradable polymers which are soluble in common organic solvents and have relatively low melting points.

It is a still further object of the present invention to prepare polymers which degrade by hydrolysis.

It is still another object of the present invention to provide a method of preparation of biodegradable polymers which is relatively inexpensive.

It is yet another object of the present invention to prepare polymers that degrade in vivo at rates suitable for controlled drug delivery.

SUMMARY OF THE INVENTION

Biodegradable polymers for biological applications, including controlled delivery of substances, are prepared from a monomer of the general formula:

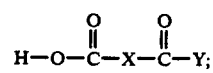

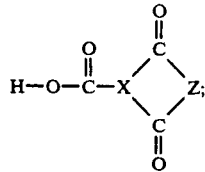

or

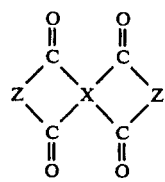

wherein X is an aliphatic or aromatic group of $C_1-C_{20}$; Y is a C-terminus peptide or proline, and Z is a C-peptide or amino acid. These polymers have a weight average molecular weight of greater than 10,000.

The monomers are prepared from amino acids or peptides which have been converted into dicarboxylic acids by reaction with aromatic or aliphatic di-, tri-, or tetracarboxylic acids or anhydrides. The resulting dicarboxylic acid monomer is polymerized under controlled conditions, particularly with respect to time and temperature of reaction, to form a poly(anhydride) which is highly pure and biocompatible.

Copolymers are prepared by the copolymerization of amido- or imido-dicarboxylic acid monomers with other dicarboxylic acids such as sebacic acid. The resulting poly(amide-co-anhydrides) and poly(imide-co-anhydrides) are useful for controlled release applications, as site-specific drug carriers, as recognition sites for adhesive proteins, as artificial organs, and for biodegradable sutures. In vivo, the anhydride linkages are hydrolytically degraded and the internal imide and amide bonds of the dicarboxylic acid are enzymatically degraded. The poly(amide-co-anhydride)s and poly(imide-co-anhydride)s have greater solubility in organic solvents and lower melting points than poly(amino acids), facilitating fabrication of controlled delivery devices.

In a preferred embodiment, a peptide to be delivered is incorporated directly into the polymer backbone and released as the polymer degrades in vivo.

DETAILED DESCRIPTION OF THE INVENTION

The present invention is a method for synthesizing polymers for biological applications, including controlled delivery of substances, and the products thereof, wherein the polymer is prepared from a monomer of the general formula:

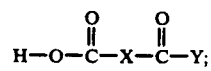

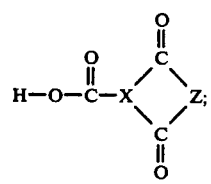

or

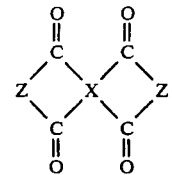

wherein X is an aliphatic or aromatic group of $C_1-C_{20}$; Y is a C-terminus peptide or proline, and Z is a C-terminus peptide or amino acid.

As used herein, a C-terminus peptide or amino acid is a peptide or amino acid which has an amino group that is covalently linked to another molecule having a carboxylic acid group which is free to react with other functional units, such as an amino acid or dicarboxylic acid.

The term amino acid refers to a molecule which has a primary or secondary amine function and a carboxylic acid function, including, but not limited to, the twenty commonly occurring α-amino acids: lysine, arginine, histidine, aspartic acid, glutamic acid, glycine, asparagine, glutamine, cysteine, serine, threonine, tyrosine, alanine, valine, leucine, isoleucine, proline, phenylalanine, methionine, and tryptophan; β-amino acids such as B-alanine, and gamma-amino acids such as gamma-amino butyric acid.

In one embodiment of the present invention, dicarboxylic acid monomers are prepared by reacting one carboxylic acid moiety of a dicarboxylic acid or anhydride with the terminal amine of proline or a peptide to form a molecule which has two terminal carboxylic acid groups and an internal amide linkage. In another embodiment, two carboxylic acid moieties of a tricarboxylic acid are reacted with the terminal amine of an amino acid or peptide to form a molecule which has two terminal carboxylic acid linkages and an internal imide bond. In another embodiment of the present invention, a tetracarboxylic acid or anhydride is reacted with two amino acid or peptide molecules to form a diimidedicarboxylic acid monomer.

The amido- or imidodicarboxylic acid prepolymers are polymerized under optimized conditions of temperature and time to yield a poly(anhydride) which is highly pure and biocompatible. The poly(anhydride) has amide and or imide linkages in the polymer backbone These polymers are termed poly(amide-co-anhydride)s and poly(imide-co-anhydride)s.

It has been experimentally determined that when a dicarboxylic acid is reacted with an amino acid which has an N-terminus primary amine, the resulting amidodicarboxylic acid does not polymerize well, presumably because the remaining hydrogen on the amide nitrogen reacts in an intramolecular cyclization reaction with the terminal carboxylic acid of the amidodicarboxylic acid or a carboxylic acid side group on the growing polymer chain. However, the procedure works well when an amino acid with an N-terminus secondary amine is used, since the resulting amidodicarboxylic acid does not have a reactive hydrogen on the amide nitrogen. An example of an amino acid with an N-terminus secondary amine that could be used to prepare dicarboxylic acid monomers according to the present invention is proline. Small peptides could also be polymerized to form amidodicarboxylic acids.

It has also been experimentally determined that when amino acids or peptides are reacted with tri- or tetracarboxylic acids, the resultant imido bonds formed prevent intramolecular cyclization in the subsequent step of polymerization. Poly(imide-co-anhydride) polymers with weight average molecular weights of greater than 100,000 have been synthesized using this method.

Polymers for controlled delivery of substances may also be formed by the copolymerization of the amido- or imidodicarboxylic acid monomers with other aromatic or aliphatic dicarboxylic acids.

The poly(amide-co-anhydride)s and poly(imide-co-anhydride)s are useful for controlled release applications, as site-specific drug carriers, as recognition sites for adhesive proteins, as artificial organs, and for biologically degradable sutures. In the first two applications, the substance to be delivered, usually a peptide, amino acid, or peptide derivative, forms a part of the polymer which is released as the polymer degrades. In vivo, the anhydride linkages of the polymers are hydrolytically degraded, followed by the slower enzymatic degradation of the N-C imide and amide bonds in the polymers.

The poly(amide-co-anhydride)s and poly(imide-co-anhydrides) have greater solubility in organic solvents and a lower melting point than poly(amino acids), allowing for easier fabrication of the polymers into shapes appropriate for controlled release devices, attachment structures or sutures.

A variety of compounds to be delivered can be incorporated into the poly(amide-co-anhydride)s and poly(imide-co-anhydrides), including amino acids such as those listed above and biologically active peptides. Examples of useful peptides are hormones, attachment peptides, and peptides that trigger a cell response. It is believed that it is not necessary to limit the peptides to lengths of three amino acids or less in order to avoid an immune response directed against the peptide since the peptide is incorporated within the polymeric matrix. In general, the polymers of the present invention can be used for controlled release of any substance which can be incorporated into the polymer backbone, such as amino acids, peptides, pseudo or derivatized amino acids, or pseudo or derivatized peptides. Further, the polymers can be used to deliver a substance which has been fabricated with the polymer. Pharmaceutical polypeptides can be incorporated into the polymer matrix, stabilizing the peptide sequence. The RGD sequence (Arg-Gly-Asp) is a well known cell recognition site for many adhesive proteins such as fibronectin, vitronectin and collagen that can be incorporated into the polymer backbone. These polymers can be used to prepare artificial organ cell scaffolds which attach cell preparations. The polymers with attached cell preparations can be implanted into animals to replace lost tissue and organ functions. See generally, Vacanti, et al., *J. Pediatric Surgery* 23(1), 3 (1988) and Pierschbacher et al., *Proc. Natl. Acad. Sci.* 80, 1224 (1983), incorporated herein by reference.

There are two variations of the method to form the polymers of the present invention. In the first, the polymers are prepared in three steps: (1) synthesis of amido- or imidodicarboxylic acid monomers; (2) diacetylation of the dicarboxcylic acids to form prepolymers; and (3) polymerization of the prepolymers by melt polycondensation. There are two steps using the second method: (1) synthesis of amido- or imidodicarboxylic acid monomers; and (2) polymerization of the unacetylated dicarboxylic acids by solution polymerization.

The methods and polymers of the present invention are further described with reference to the following non-limiting examples.

EXAMPLE 1

Preparation of Amido- and Imidodicarboxylic Acid Monomers

Dicarboxylic acid monomers are prepared by condensation of equimolar amounts of a di- or tricarboxylic acid or anhydride molecule with an amino acid or peptide or by condensation of a tetracarboxylic acid or anhydride with two equivalents of an amino acid or peptide. Alternatively, the diacids can be prepared by cross-imidation of N,N'-dicarboethoxypyromellitic diimide.

Examples of suitable polycarboxylic acids and anhydrides include 1,2,4-benzenetricarboxylic acid (trimellitic acid), trimellitic anhydride (TMA), 1,2,4,5-benzenetetracarboxylic acid (pyromellitic acid), pyromellitic dianhydride (PMDA), maleic acid, maleic anhydride, malonic acid, succinic acid, succinic anhydride, and fumaric acid.

The reaction of TMA and PMDA with amino acids to form imidodicarboxylic acids and diimidodicarboxylic acids has been described by Gonzalez, et al., *Die Angewandte Makromolekulare Chemie* 55, 85 (1976). In general, the poly(carboxylic acid) and amino acid or peptide are mixed in an appropriate organic solvent such as N,N'-dimethylformamide (DMF) or m-cresol. The solution is heated at reflux for one to five hours with stirring, with or without nitrogen. The solution is then concentrated and the product is extracted several times with diethyl ether. The product crystallizes from the solution, and is recrystallized in water.

When m-cresol is used as the solvent, the product precipitates on cooling without the need to extract into ether. Other solvents for preparation of the prepolymers include chloroform, tetrahydrofuran, and DMF.

The reaction of maleic and succinic anhydride with amino acids or peptides to form amido-dicarboxylic acids is described in Japanese Patent No. 81 12,351 (Chem. Abstract 95:62702a, 1981). For example, the anhydride and amino acid or peptide are heated in an inert organic solvent at reflux for one to five hours, and then isolated and purified according to procedures known to those skilled in the art.

Cross-imidation of N,N-dicarboethoxypyromellitic diimide with amino acids or peptides to form a diimidedicarboxylic acid is accomplished by mixing the N,N-dicarboethoxy pyromellitic diimide with the desired amino acid or peptide in water, and stirring the solution at room temperature or slightly elevated temperature until the diimide goes into solution. After filtration and acidification of the reaction mixture, the product is isolated and purified.

Other imidodicarboxylic acids and amidodicarboxylic acids can be prepared by the above described procedures or modifications thereof.

Preparation of N-succinyl-proliner

A mixture of proline (3 g, 26.1 mmol) and succinic anhydride (2.87 g, 28.7 mmol) was stirred in tetrahydrofuran (20 ml) at 65° C. for 4 hours. The resulting solution was filtered and concentrated. The crude material was then dissolved in a small amount of anhydrous diethyl ether and placed at −20° C. to crystallize overnight. The resulting prepolymer has a melting point ca. 95° C.; IR 1770, 1700, 1620 cm-1.

Preparation of N-trimellitylimido-glycine

Glycine (1 g, 13.3 mmol) and trimellitic anhydride (2.56 g, 13.3 mmol) were heated at reflux in dimethylformamide (15 ml) for 4 hours. The reaction mixture was cooled, filtered, and the solution was concentrated. The crude product was extracted twice with anhydrous diethyl ether and then stored at −20° C. to crystallize. The crystals can also be recrystallized from water and dried under vacuum at 120° C. Table 1 provides the melting point and infrared data for N-trimellitylimido-glycine, N-trimellitylimido-$\beta$-alanine, N-trimellitylimido-gamma-aminobutyric acid, and N-trimellitylimido-triglycine prepared according to this procedure.

TABLE 1

| Amino Acid | N-trimellitylimido-glycine, N-trimellitylimido-$\beta$-alanine, N-trimellitylimido-$\gamma$-aminobutyric acid, and N-trimellitylimido-triglycine. | |
|---|---|---|
| | melting point (°C.) | IR (cm$^{-1}$) |
| Glycine | 268 | 1780(w), 1705(s) |
| $\beta$-Alanine | 245 | 1780(w), 1700 |
| $\gamma$-Amino butyric acid | 220 | 1780(w), 1700, 1690 |
| Triglycine | 260 | 1780(w), 1730, 1720, 1700, 1650, 1640 |

EXAMPLE 2

Preparation of Prepolymers

As used herein, the term prepolymer refers to an amidodicarboxylic acid or imidodicarboxylic acid which has been diacetylated. Prepolymers of amido- and imidodicarboxylic acids are prepared by heating at reflux the dicarboxylic acids in excess acetic anhydride for a time period of approximately 10 min to 3 hours. The acetic anhydride is then removed under vacuum at 40° C. The oily crude material is dissolved in either anhydrous toluene or diethyl ether, or other appropriate solvent, and left to solidify at −20°C. The crystals are filtered off and stirred in diethyl ether. After filtration the pure crystals are dried under vacuum.

Prior methods of preparing the diacetyl prepolymers describe reaction times of 12 to 16 hours at reflux. These reaction conditions are not suitable when preparing polymers for use in controlled drug delivery devices because of the potential for side reactions which reduce the purity of the resulting polymer and may affect the biocompatibility of the polymer.

Preparation of Prepolymer of N-Trimellitylimido-glycine

N-Trimellitylimido-glycine (11.8 g) was added to acetic anhydride (200 ml) and heated at reflux under dry nitrogen sweep for 2 hours. The solution was filtered and concentrated. Anhydrous toluene (4 ml) was added and the solution was left at −20° C. to crystallize overnight. The crystals were separated by filtration and stirred in anhydrous ether for several hours. The white crystals were separated by filtration and lyophilized to dryness.

The prepolymer can also be synthesized under milder conditions, i.e., at lower temperatures. The lower the temperature, the more time is needed for the reaction to occur.

Table 2 describes the melting point and infrared data for prepolymers prepared according to this procedure from the listed amino acids and peptides.

TABLE 2

| | N-Trimellityl Amino Acid Prepolymers. | |
|---|---|---|
| Prepolymers | melting point (°C.)* | IR (cm$^{-1}$) |
| Glycine | 70–80 | 1825, 1800, 1730, 1710 |
| $\beta$-Alanine | 70–80 | 1815, 1790, 1720, 1700 |
| $\gamma$-Amino butyric acid | 70–80 | 1810, 1780, 1720 |

*melting points vary slightly, depending on the chain length of the prepolymers.

EXAMPLE 3

Preparation of Polymers

Poly(amide-co-anhydride)s and poly(imide-co-anhydride)s are prepared by melt polycondensation of diacetylated prepolymers or solution polymerization of the unacetylated dicarboxylic acids.

Melt Polycondensation

Prepolymers prepared as described above are placed in a Kimax glass tube with a side arm equipped with a capillary nitrogen inlet. The tube is immersed in an oil bath at the selected temperature (100°–200° C.). After the prepolymers melt, high vacuum is applied and the condensation by-product, acetic anhydride, is trapped in an acetone/dry ice trap. The crude polymer is dissolved in a small amount of dichloromethane and is then slowly added to excess petroleum ether, which causes the polymer to precipitate.

In another embodiment of the present invention, imidodicarboxylic acid, amido-dicarboxylic acid, or diimidodicarboxylic acid is co-polymerized with other dicarboxylic acids of the general formula

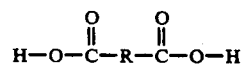

wherein R is an aromatic or aliphatic group of $C_1$–$C_{20}$. Examples of R include alkyl, alkenyl, alkynyl, aromatic or heteroaromatic groups, such as furan, tetrahydrofuran, thiophen, or 1-methylpyrrole.

The copolymers are prepared by mixing prepolymers of the desired monomers in desired ratios and then proceeding with the melt polymerization reaction as described above. For example, a diacetylated imido-dicarboxylic acid can be mixed with diacetylated sebacic acid examples of which are listed in Table 3.

It is sometimes desirable to include a dicarboxylic acid comonomer to improve the physical properties of the polymer for biological applications. For example, the homopolymers of N-trimellityllimidoamino acids are very rigid, brittle and typically have a low molecular weight (<10,000). Copolymerization with sebacic acid improves molecular weight (weight average Mw>20,000), tensile strength and elasticity. Fibers melt-drawn from these copolymers preserve their elasticity over long periods of time, indicating that the fibers are suitable as bioabsorbable suture materials.

Table 3 provides the highest molecular weight attained for polymers containing various ratios of N-trimellitylimido glycine and sebacic acid, polymerized over a range of temperatures and reaction times. As shown, a molecular weight of almost 105,000 is attained after 1.5 hours with a monomer mix of 16% N-trimellitylimido glycine to sebacic acid at a temperature of 160° C. The molecular weights of the polymers were determined by gel permeation chromatography.

Other factors such as the temperature of polymerization, time of polymerization and use of catalysts influence the molecular weight and physical characteristics of the resulting polymer. One of the most important factors affecting polymerization is the temperature of reaction. Polymers for controlled drug delivery must be of high molecular weight to provide appropriate degradation rates and profiles in vivo, and at the same time be of sufficient purity that the polymer does not invoke an immune response. Polymerization temperatures greater than 200° C. lower the final molecular weight of the polymer and increase the degree of side reactions and polymer degradation. For these reasons, methods for the melt polycondensation of imido-dicarboxylic acids such as that of Gonzalez, et al., *Die Angewandte Makromolekulare Chemie* 55, 85 (1976), which describes temperatures of polymerization ranging from 220°-290° C., are not suitable for the preparation of a poly(amide-co-anhydride) or poly(imide-co-anhydride) for biological applications. Polymers made according to the method of Gonzales are generally of low molecular weight. In addition, not all reaction intermediates in this procedure are purified before polymerization, further diminishing the biocompatibility of the final polymer.

Another factor which affects the molecular weight of the polymer is the use of catalysts. The most effective catalysts are the earth metal oxides, such as barium oxide, calcium oxide, calcium carbonate, bismuth oxide, and antimony oxide, and the metal salts, such as lead acetate and cadmium acetate.

For example, melt polycondensation of N-trimellitylimido glycine results in a MW of 19,760 at 150° C. without a catalyst after 100 minutes compared with a MW of 38,820 obtained with 1 mol % of BaO under the same conditions. The use of catalysts is therefore preferred for the preparation of polymers from thermally sensitive monomers.

TABLE 3

Weight Average Molecular Weights for Polymers containing various Ratios of N-trimellityllimido glycine to sebacic acid

| Percent TMA-Gly | Percent Sebacic Acid | Catalyst | Temp (°C.)/ Time (h) | Highest Weight Average MW/Time (h) |
|---|---|---|---|---|
| 16 | 84 | | 160/3 | 104860/1.5 |
| 16 | 84 | | 180/3 | 123715/2 |
| 16 | 84 | | 120/3.5 | 35610/2.33 |
| 20 | 80 | | 100/6 | 31480/6 |
| 20 | 80 | 1 mol % Cd(ac)₂ dry | 100/4.5 | 21580/4.33 |
| 20 | 80 | 1 mol % BaO | 150/3 | 55545/2.5 |
| 20 | 80 | | 180/45 min | 30420/45 min |
| 20 | 80 | 1 mol % Pb(ac)₂ dry | 180/45 min | 61880/45 min |
| 22 | 78 | | 150/3.75 | 38785/3.58 |
| 34 | 66 | | 160/3.5 | 23400/3 |
| 39 | 61 | | 150/2.5 | 18940/2.5 |
| 50 | 50 | | 180/30 min | 10150/30 min |
| 50 | 50 | | 180/30 min | 13520/30 min |
| 50 | 50 | 1 mol % Pb(ac)₂ dry | 180/30 min | 14500/30 min |
| 50 | 50 | | 160/3 | 18495/2 |
| 65 | 35 | | 160/3 | 10010/3 |
| 66 | 34 | | 160/3 | 3180/2.5 |

TABLE 3-continued

Weight Average Molecular Weights for Polymers containing various Ratios of N-trimellityllimido glycine to sebacic acid

| Percent TMA-Gly | Percent Sebacic Acid | Catalyst | Temp (°C.)/ Time (h) | Highest Weight Average MW/Time (h) |
|---|---|---|---|---|
| 20 | 80 | 1 mol % Bi₂O₃ | 180/4.25 | 13640/3 |

Preparation of TMA-Gly:SA polymer

Diacetylated N-trimellitylimido-glycine (1 g, 3.55 mmol) was mixed with diacetylated sebacic acid (2.7 g, 14.2 mmol) (mole ratio 20:80), and with 1-2 mole % of a catalyst in a Kimax glass tube (2×20 cm, Kimax) with a side arm equipped with a capillary nitrogen inlet. Under nitrogen sweeps the tube was immersed in an oil bath at a defined temperature, either 100°, 120°, 150°, or 180° C. After the polymers were melted, high vacuum ($>10^{-2}$ millitorr) was applied through the side arm. The condensation by-product, acetic anhydride, was collected in an acetone/dry ice trap. The reaction time varied with the different temperatures and catalysts. At the end of the polymerization, the polymer was removed, dissolved in methylene chloride or chloroform (30 ml), filtered and precipitated into petroleum ether (ca. 300 ml). The precipitate was collected and washed with anhydrous ether. The resulting polymer had a melting point of 67° C. and IR maxima of 1810,1730 $cm^{-1}$.

Poly(N-trimellitylimido-glycine-co-sebacic acid) at mole ratios of 16:84 and 22:78 imidodicarboxylic acid to sebacic acid and poly(N-trimellitylimido-β-alanine-co-sebacic acid) were also prepared according to this procedure. Poly(N-trimellitylimido-glycine-co-sebacic acid) (16:84) melt polymerized at 120° C. had the following characteristics: GPC: $M_w=35608$, $M_n=12900$, $M_w/M_n=2.76$. $^1$H-NMR (CDCl$_3$,δ): 8.5 (m,2H), 8.04 (d, 1H, J=7.85), 4.59 (s, 2H), 2.67 (t, 4H, J=7.3), 2.53, t, 4H, J=7.3), 2.44 (t, 4H, J=7.4), 1.65 (m, 4H), 1.32 (s, 8H). IR (CHCl$_3$, $cm^{-1}$): 2930, 2860 (C—H), 1810 (C=O, anhydride), 1730 (N—C=O, imide). Anal. Calcd.: C, 63.69; H, 7.52: N, 1.14. Found: C, 62.76; H, 7.32; N, 1.17.

Poly(N-trimellitylimido-glycine-co-sebacic acid) (22:78) melt polymerized at 150° C. had the following characteristics: GPC: $M_w=38783$, $M_n=12277$, $M_w/M_n=3.159$. $^1$H-NMR (CDCl$_3$,δ): 8.52 (s, 1H), 8.48 (d, 1H, J=8), 8.04 (d, 1H, J=7.8), 4.59 (s, 2H), 2.67 (t, 4H, J=7.3), 2.53 (t, 4H, J=7.3), 2.44 (t, 4H, J=7.35), 1.68 (m, 4H), 1.3 (m, 8H). IR (KBr, $cm^{-1}$): 2920, 2850 (C—H), 1810 (C=O, anhydride), 1730 (N—C=O, imide). Anal. Calcd.: C, 63.04; H, 695; N, 1.61. Found: C, 62.14; H, 6.71; N, 2.02.

Poly(N-trimellitylimido-β-alanine-co-sebacic acid) (16:84) melt polymerized at 120° C. with 2 mol % CaCO$_3$ had the following characteristics: GPC: $M_w=91582$, $M_n=31786$, $M_w/M_n=2.881$. $^1$H—NMR (CDCl$_3$),δ): 8.44 (m, 2H), 7.98 (d, 1H, J=7.7), 4.07 (t, 2H, J=6.88), 2.93 (t, 2H, J=6.85), 2.67 (t, 4H, J–7.25), 2.44 (st,f 4H, J=7.27), 1.65 (m, 4H), 1.3 (s, 8H). $^{13}$C—NMR (CDCl$_3$): 169.5, 168.7, 168.3, 166.5, 136.2, 135.9, 134.4, 132.4, 124.9, 123.8, 123.5, 35.4, 35.1, 33.9, 33.5, 28.8, 28.6, 24.5, 24.1, 23.2 IR (KBr, $cm^{-1}$): 2930, 2860 (C—H), 1810 (C=O, anhydride), 1730 (N—C=O, imide). Anal. Calcd.: C, 63.95; H, 7.53; N, 1.14. Found: C, 62.49; H, 7.28; N, 1.4.

solution Polymerization

Solution polymerization of polyanhydrides is described by Domb, Ron, and Langer in *Macromolecules* 21, 1925 (1988), incorporated herein by reference.

In general, dicarboxylic acids can be polymerized with sebacoyl chloride, phosgene, or diphosgene as the coupling agent and either poly(4-vinylpyridine) or K₂CO₃ as the insoluble acid acceptor. The polymer is soluble in the reaction solution and the only by-product formed is the insoluble acid acceptor-hydrochloride salt. The following working example further illustrates the method using solution polymerization.

The coupling agent (e.g., phosgene or diphosgene) was added dropwise to a stirred solution of imide-dicarboxylic acid or amide-dicarboxylic acid diacid and tertiary amine base in an organic solvent. The reaction mixture was stirred for several hours at 25° C. The insoluble solids (e.g., PVP.HCl) were removed by filtration. The polymer was precipitated by dripping the filtrate into excess petroleum ether. The precipitated polymer was isolated by filtration and dried in a vacuum oven for 24 hours at 40° C. When either triethylamine (TEA) or pyridine were used, the polymerization reaction was quenched in petroleum ether and the polyanhydride precipitated from solution.

This invention has been described with reference to its preferred embodiments. Variations and modifications of the present invention will be obvious to one of ordinary skill in the art from the foregoing detailed description of the invention. It is intended that all of these variations and modifications be included within the scope of the appended claims.

We claim:

1. A biocompatible, biodegradable polymer produced from monomers selected from the group consisting of

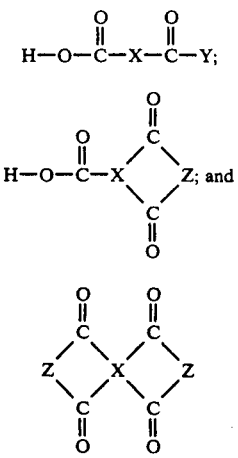

wherein X is an aliphatic or aromatic group of $C_1$–$C_{20}$; Y is a C-terminus peptide or proline, and Z is a C-terminus peptide or amino acid, and having a weight average molecular weight of greater than 10,000.

2. The polymer of claim 1 wherein the monomer is selected from the group consisting of N-succinyl-proline, N-succinyl-peptide, N-trimellitylimido-amino acid, N-trimellitylimido-peptide, N,N-pyromellityldiimido-amino acid, and N,N-pyromellityldiimido-peptide.

3. A device formed of the polymer of claim 1 for controlled delivery of a biologically active substance.

4. A bioabsorble suture of the polymer of claim 1.

* * * * *